United States Patent [19]

Shroff

[11] 4,146,024
[45] Mar. 27, 1979

[54] INTRA CERVICAL CONTRACEPTIVE DEVICE

[76] Inventor: Behzad D. Shroff, P.O. Box 448, Fremantle, Western Australia, Australia, 6160

[21] Appl. No.: 799,108

[22] Filed: May 20, 1977

[30] Foreign Application Priority Data

Jun. 1, 1976 [AU] Australia .................. 6132/76

[51] Int. Cl.² .............................................. A61F 5/46
[52] U.S. Cl. ............................................... 128/131
[58] Field of Search ............................ 128/127–131, 128/260

[56] References Cited

U.S. PATENT DOCUMENTS 2,836,177  5/1958  Sells .................... 128/127

FOREIGN PATENT DOCUMENTS 205041 12/1908  Fed. Rep. of Germany .......... 128/131
269562  1/1914  Fed. Rep. of Germany .......... 128/131
587231 11/1933  Fed. Rep. of Germany .......... 128/131

Primary Examiner—Lawrence W. Trapp
Attorney, Agent, or Firm—James C. Wray

[57] ABSTRACT

An intracervical contraceptive device comprising a tubular member open at each end and adapted to be positioned in the cervical canal and having a valve member incorporated therein which allows body fluids to pass from the uterine cavity into the vagina but not in the reverse direction.

7 Claims, 3 Drawing Figures

INTRA CERVICAL CONTRACEPTIVE DEVICE

This invention relates to an intracervical contraceptive device.

In one form the invention resides in an intracervical contraceptive device comprising a tubular member open at each end and adapted to be positioned in the cervical canal and having a valve member incorporated therein which allows body fluids to pass from the uterine cavity into the vagina but not in the reverse direction.

Preferably the device is provided with a member which projects into the uterine cavity to prevent accidental dislodgement of the device.

The invention will be better understood by reference to the following description of the specific embodiments thereof shown in the accompanying drawings wherein.

Figure 1:
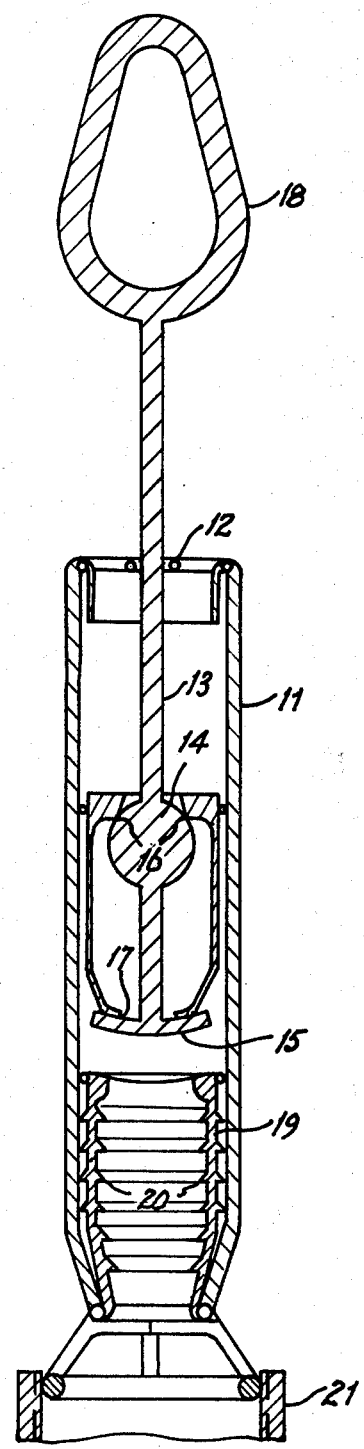
FIG. 1 is a sectional elevation of one embodiment.

In the embodiment shown in FIG. 1 of the drawings a tubular member 11 is open at each end, the upper end being provided with a collar 12 through which a valve stem or rod 13 is slidably mounted. The lower end of the valve rod 13 is provided with a spherical valve member 14 and a dished valve member 15 each adapted to seat on valve seats 16 and 17 respectively positioned within the tubular member 11. The upper end of the valve stem or rod 13 is provided with an enlargement 18. A sleeve 19 provided with inwardly directed projections 20 may be fitted into the lower end of the tubular member. Preferably the lower end of the tubular member is externally threaded so that it can be engaged by an internally threaded cup like section 21 of the inserting unit. A short length of silk or like thread (not shown) may be fitted to the lower end of the tubular member to facilitate withdrawal of the device.

The device is fitted into the cerival canal with the enlargement 18 projecting into the uterine cavity and the inserting unit unscrewed. When in position the device will prevent sperm passing upwardly through the tubular member to enter the uterine cavity. The projections 20 on the sleeve 19, if fitted, serves to hinder the movement of the sperm. Any body fluids produced in the uterine cavity are able to pass downwardly through the tubular member into the vagina for discharge in the usual manner.

The device is preferably formed from copper but it may be formed from other metals or metal alloys compatible with body tissues including copper, silver, zinc, cobalt, aluminium, titanium and stainless steel or from suitable plastic materials such as "Teflon."

If desired the ball valve 14 may be replaced by a disc valve.

Figure 2:
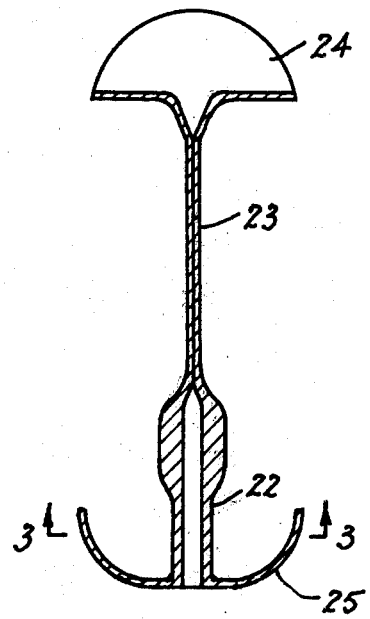
FIG. 2 is a sectional elevation of a second embodiment.
Figure 3:
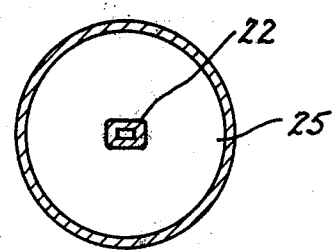
FIG. 3 is a section on line 3—3 of FIG. 2.

The embodiment shown in FIG. 2 of the drawings is formed entirely from platic such as a silicone elastomer or other plastics which are compatible with body tissues and fluids such as those used for the manufacture of contact lenses. The device comprises a short tube 22 which merges with a flattened section 23 the walls of which are normally in contact. The free end of the short tube is provided with an outwardly projecting flange 24 whilst the free end of the flattened section is provided with an outwardly projecting flange 25 which is so shaped that it closely fits the cervix.

To insert the device an inserter not shown is threaded through the short tube 22 and the flattened section 23 so that it projects beyond the upper end of the device. The inserter is then inflated with air or water so that the assembly becomes more or less rigid. The projecting end of the inserter preferably assumes a mushroom shape when inflated to provide a cover for the flange 24. The assembly is then inserted into the cervix until the flange 24 is located in the lower segment of the uterus. The inserter is then deflated and withdrawn through the device. The flange 24 holds the device in position. The walls of the flattened section 23 remain in contact in the closed position unless there is a build up of body fluids in the uterus to provide a pressure gradient sufficient to force the walls apart and allow the fluids to escape. Normally the pressure of any fluids endeavouring to pass upwardly into the uterus is not sufficient to force the walls apart.

What I claim is:

1. An intracervical contraceptive device comprising a tubular member open at each end and adapted to be positioned in the cervical canal and having a valve member incorporated therein which allows body fluids to pass from the uterine cavity into the vagina but not in the reverse direction, wherein the upper end of the tubular member is provided with a collar through which a valve stem or rod slidably passes, the upper end of the stem or rod being provided with an enlargement and the lower end of the rod being provided with a spherical valve member which seats on a valve seat located with the tubular member.

2. A device as claimed in claim 1 wherein a dished valve member is located below the spherical valve member to seat on a second valve seat located within the tubular member.

3. An intracervical contraceptive device comprising a tubular member open at each end and adapted to be positioned in the cervical canal and having a valve member incorporated therein which allows body fluids to pass from the uterine cavity into the vagina but not in the reverse direction, wherein a sleeve provided with internally directed projections is fitted into the tubular member below the valve.

4. An intracervical contraceptive device comprising a tubular member open at each end and adapted to be positioned in the cervical canal and having a valve member incorporated therein which allows body fluids to pass from the uterine cavity into the vagina but not in the reverse direction, wherein tubular member is formed of plastic and the upper portion is flattened so that the walls normally lie together in contact to form the valve member.

5. A device as claimed in claim 4 wherein the tubular member is provided at its upper end with an outwardly projecting flange.

6. A device as claimed in claim 1 wherein a sleeve provided with internally directed projections is fitted into the tubular member below the valve.

7. An intracervical contraceptive device comprising a tubular member open at each end and adapted to be positioned in the cervical canal and having a valve member incorporated therein which allows body fluids to pass from the uterine cavity into the vagina but not in the reverse direction and is provided with a member which projects from the valve member into the uterine cavity to prevent accidental dislodgement of the device.

* * * * *